United States Patent [19]
Yoon

[11] Patent Number: 4,869,268
[45] Date of Patent: Sep. 26, 1989

[54] MULTI-FUNCTIONAL INSTRUMENTS AND STRETCHABLE LIGATING AND OCCLUDING DEVICES

[76] Inventor: InBae Yoon, 2101 Highland Ridge Dr., Phoenix, Md. 21131

[21] Appl. No.: 257,202

[22] Filed: Oct. 13, 1988

Related U.S. Application Data

[62] Division of Ser. No. 49,503, May 14, 1987, Pat. No. 4,788,966.

[51] Int. Cl.$^4$ ............................................. A61B 19/00
[52] U.S. Cl. ....................................... 128/831; 128/326
[58] Field of Search ...................... 128/831, 335.5, 325, 128/326, 346

[56] References Cited

U.S. PATENT DOCUMENTS

| | | | |
|---|---|---|---|
| 3,858,571 | 1/1975 | Rudolph | 128/831 |
| 3,870,048 | 3/1975 | Yoon | 128/4 X |
| 3,911,923 | 10/1975 | Yoon | 128/303 A |
| 3,918,431 | 11/1975 | Sinnreich | 128/831 |
| 3,989,049 | 11/1976 | Yoon | 128/303 A X |
| 4,135,495 | 1/1979 | Borgen | 128/831 |
| 4,548,201 | 10/1985 | Yoon | 128/326 |
| 4,681,110 | 7/1987 | Wiktor | 128/325 X |
| 4,788,966 | 12/1988 | Yoon | 128/831 |

*Primary Examiner*—William H. Grieb

[57] ABSTRACT

A multi-functional surgical device useful, for example, for male and female sterilization procedures. The device can be used for applying an elastic occluding ring onto an anatomical tubular structure, for cutting and cauterizing the cut ends of such a structure, for introducing a gas and/or anesthesia into the surgical field, for a biopsy procedure, for illuminating and viewing the surgical field, for applying a conventional clip to an anatomical tubular structure, and/or for applying a flexible and resilient ligature. An applicator device for applying a flexible and resilient ligature, plug or cap onto an anatomical tubular structure including tissue grasping forceps moved into and out of the distal end of a tubular member which has one or two anatomical tubular structure receiving slots. A flexible and resilient ligature, plug or cap having legs and a base having sufficient elastic memory to close the legs and occlude an anatomical tubular structure.

3 Claims, 8 Drawing Sheets

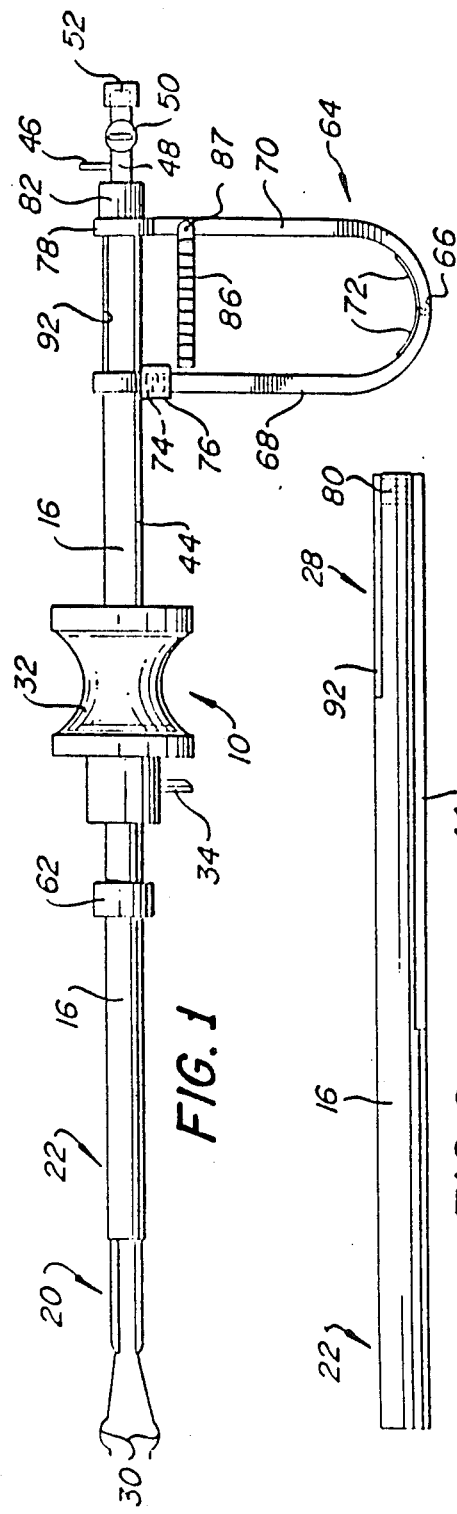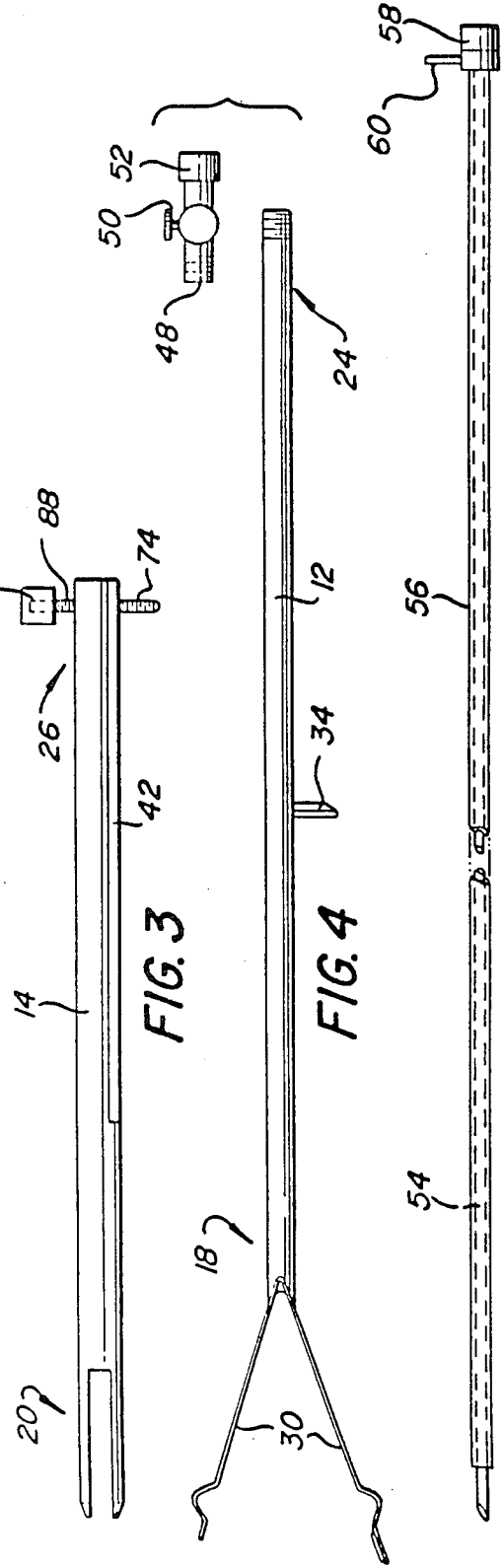

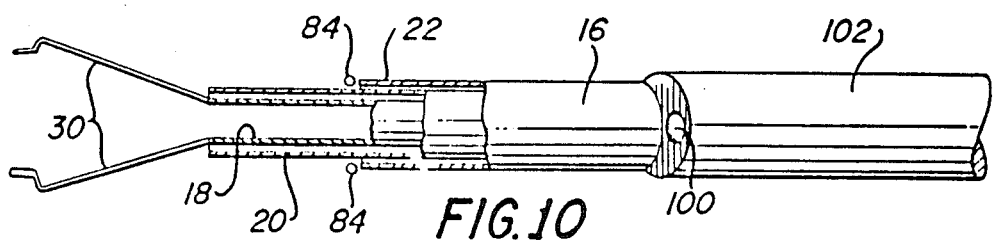
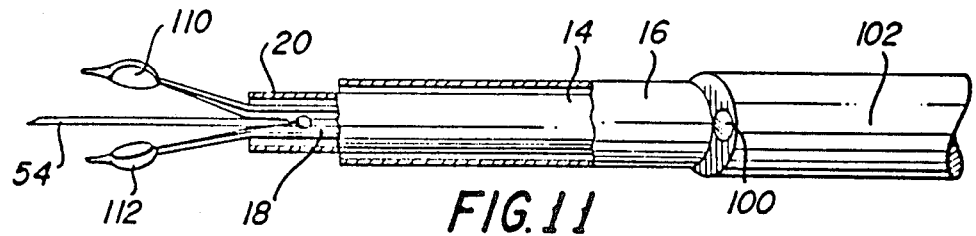
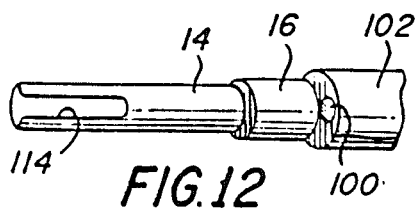 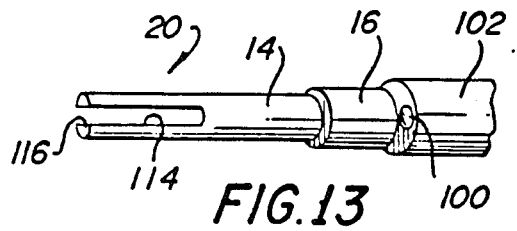
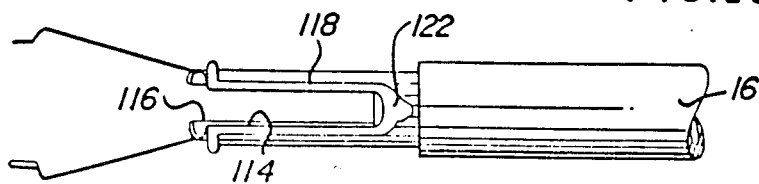
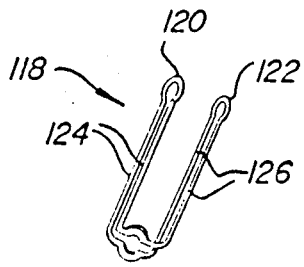 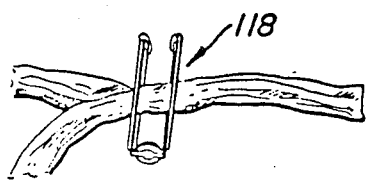

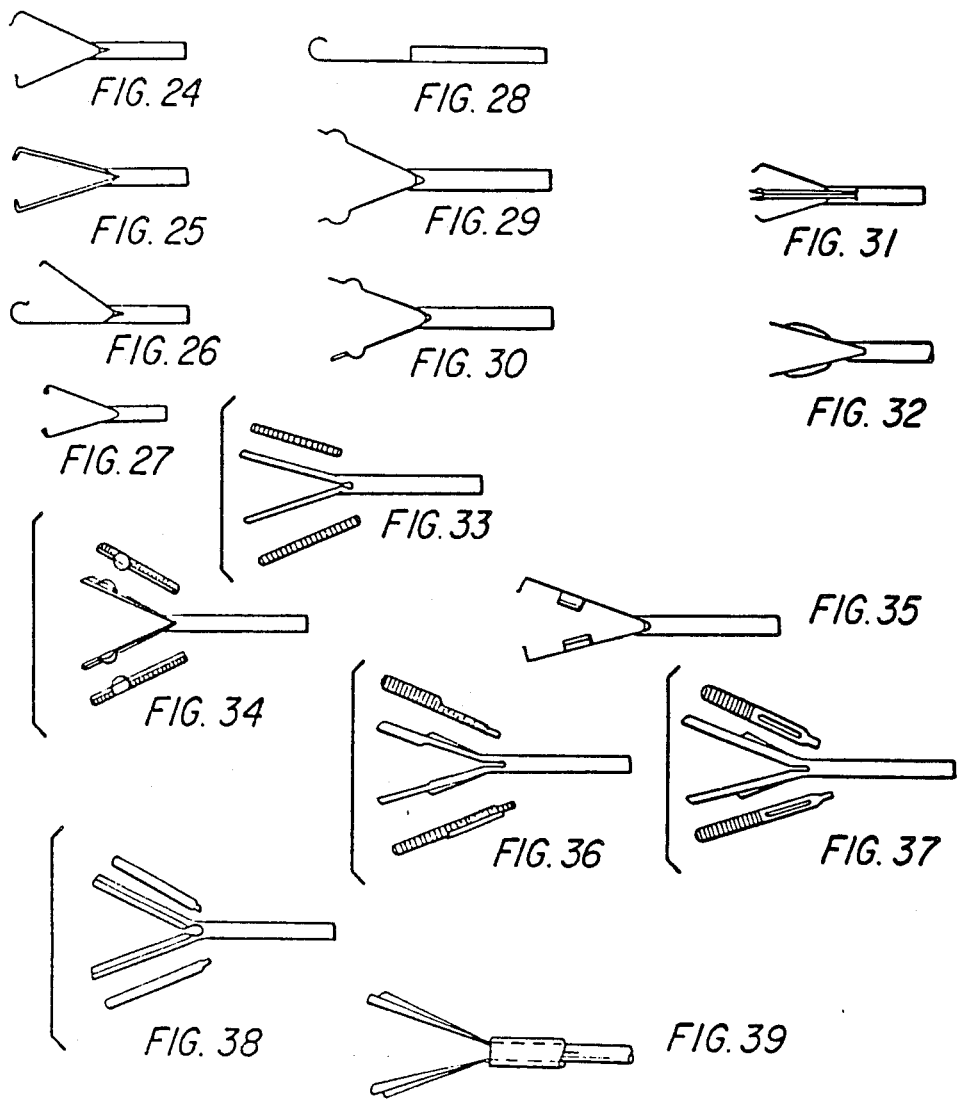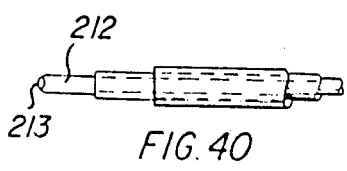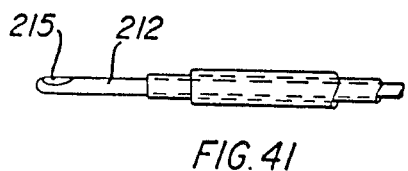

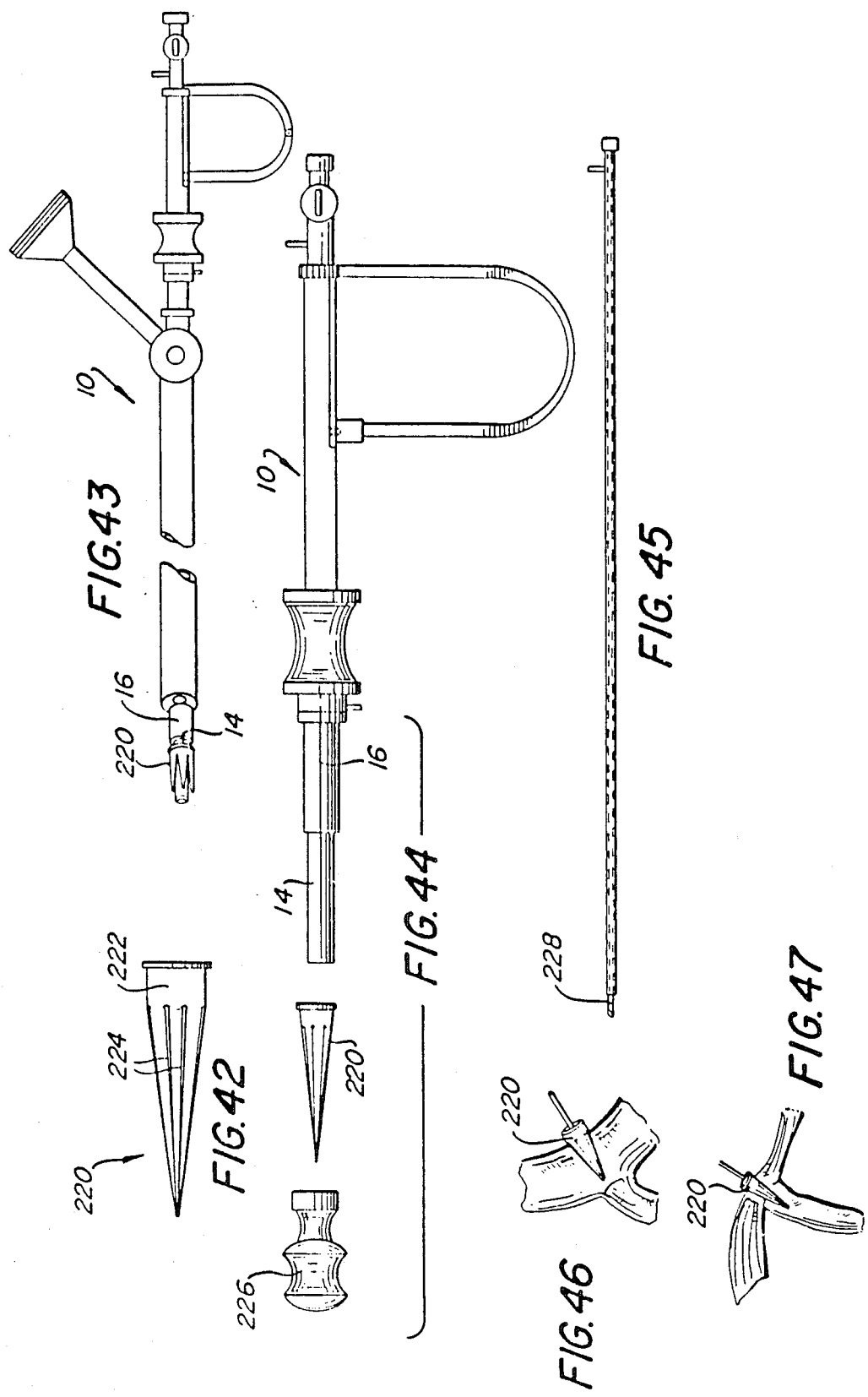

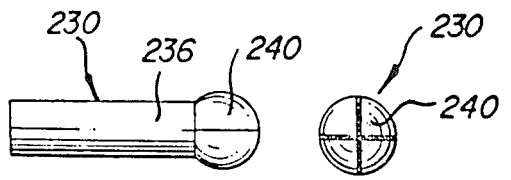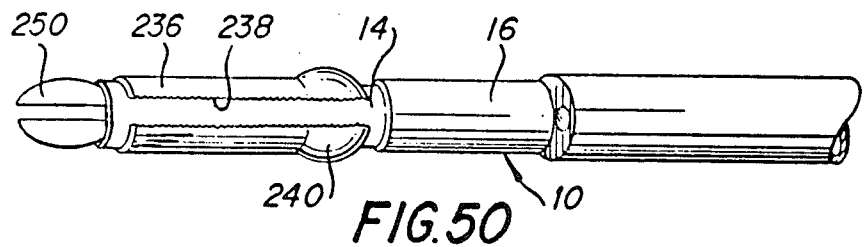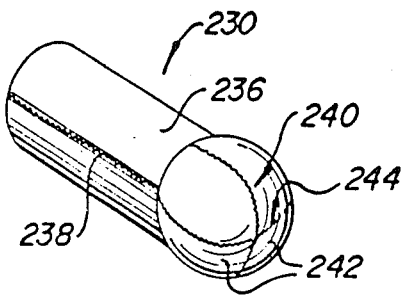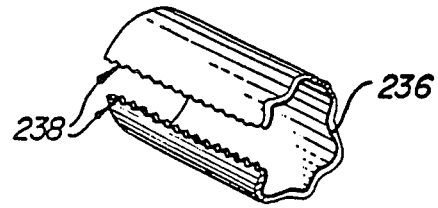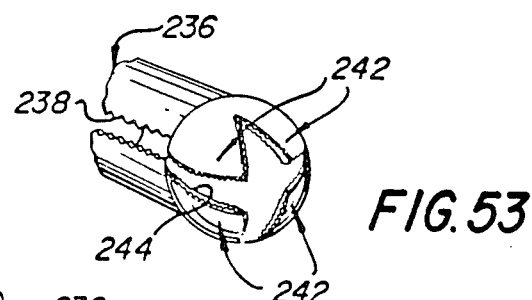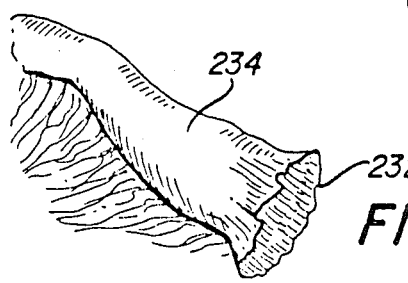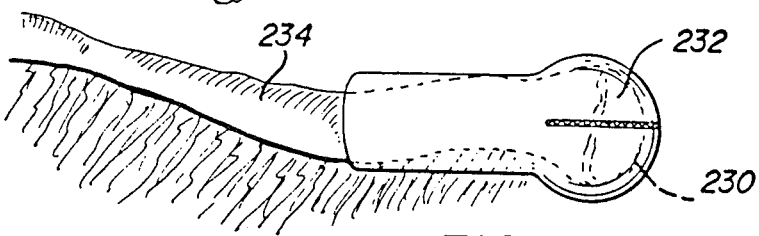

MULTI-FUNCTIONAL INSTRUMENTS AND STRETCHABLE LIGATING AND OCCLUDING DEVICES

This application is a division of application Ser. No. 049,503 filed May 14, 1987, now U.S. Pat. No. 4,788,966.

This invention relates generally to surgical devices and instruments, and, more particularly, to a multi-functional endoscopic and/or non-endoscopic surgical device, which may be used to accomplish all phases of applying an occluding ligature to an anatomical tubular or non-anatomical tubular organ structure. For example, the invention may be used to occlude or sever the Fallopian tubes of a female or the vas deferens of a male, or for vascular ligation, plugging anatomical lumen or encapsulating organ tissue structure.

Currently, there are numerous practices employed to effect sterilization in women and men. One practice is to cut and tie the Fallopian tubes. Another practice is the use of an endoscope through which the Fallopian tubes can be electrically coagulated by a bipolar or unipolar instrument. Another practice is the use of a permanently deformable clip or elastic ring for clipping or occluding the tubes, vas deferens or blood vessels. Clipping and occluding procedures are potentially reversible sterilization by application of one or more clips to the Fallopian tubes or one or more elastic rings to loops formed in the Fallopian tubes or vas deferens. Means and methods for accomplishing this procedure with elastic rings are fully disclosed in my previous U.S. Pat. Nos. 3,870,048, 3,911,923, 3,989,049, the teachings of which are incorporated herein by reference, and others. The electric unipolar or bipolar technique involves electrical cauterization of the Fallopian tubes, vas deferens or blood vessels. Each of these procedures has its own, well known attendant advantages and disadvantages. The electric technique has less chance of reversibility of the Fallopian tubes or vas deferens than clipping or occluding by elastic ring by way of tuboplasty (end to end anastomosis).

Prior to the instant invention, there was no multi-purpose instrument or device which could be used to accomplish any one of the sterilization techniques just noted above, and the attendant procedures of applying anesthesia, injection of an inert gas such as carbon dioxide into the surgical field, taking a biopsy, applying suction, etc. Furthermore, the prior art technique of applying clips to effect sterilization employed clips which were permanently deformable in order to occlude the tubes. The use of a spring loaded clip having sufficient elastic memory to completely occlude the tubes once in place was heretofore unknown.

In summary, the electric coagulation technique, clip technique and ring technique have their own advantages and disadvantages which are also related to the individual patient's age and condition of the Fallopian tubes. In order to utilize the advantages of the above-mentioned three major types of laparoscopic (endoscopic) tubal ligation and eliminate the disadvantages of these three techniques, the instrument of the present invention can apply selectively all three techniques depending on the individual circumstances at the time of the surgical procedure, and also can effect reversible sterilization without tuboplasty (in other words, by simple removal of the occluding devices, patients can be restored to their fertility stages). There are two reversible sterilization techniques in addition to the above-mentioned techniques which are plugging the utero-tubal junction through the hysteroscope and Fimbrial encapsulation, both of which can be accomplished with the instrument of the present invention. This new and improved instrument used with various occluding devices offers not only permanent or reversible sterilization but also various other endoscopic surgical procedures such as vascular ligation, polypectomy and other ligating, clipping, plugging and/or encapsulating surgical procedures.

SUMMARY OF THE INVENTION

Accordingly, it is a principal object of this invention to provide a multi-purpose surgical device for occluding an anatomical tubular structure by any of the presently known techniques, the device being further useful to accomplish all the ancillary procedures to accomplish occlusion of an anatomical tubular structure (e.g., sterilization).

It is a further object of the invention to provide an improved, flexible and resilient or stretchable ligature for an anatomical tubular structure which has sufficient elastic memory to accomplish occlusion once released around or across an anatomical structure, such as the Fallopian tubes or vas deferens.

It is another object of the invention to provide an improved, multi-functional surgical device for occluding an anatomical tubular structure which is further combined with illumination and viewing means (e.g., a laparoscope), the viewing means including a swivel connection to the multi-functional surgical device, thereby rendering the entire structure far easier to use in accomplishing a surgical procedure.

Yet another object of the invention is to provide a surgical device to accomplish sterilization by any one of a wide variety of methods, such as electrical cauterization, cutting and tying the tubes, occlusion of tubes, plugging the utero-tubal junction or Fimbrial encapsulation, by application of a clip, plug, or elastic ring, or application of a shape-retaining, stretchable clip.

Still another object of the invention is to provide a new and improved stretchable clip for occluding an anatomical tubular structure, the clip or ligature having sufficient elastic memory so as to grasp and firmly occlude the anatomical tubular structure after release from an opened, distended state.

A further object of the invention is to provide such an improved, multi-functional surgical device having interchangeable forceps for various surgical applications.

BRIEF DESCRIPTION OF THE DRAWINGS

Further and more complete objects and advantages of the invention will become readily apparent by reference to the following drawings in which:

FIG. 1 is a side, elevational view of a preferred embodiment of the surgical device of this invention;

FIG. 2 is a side, elevational view of the outer tube or cylinder of the device shown in FIG. 1, drawn to an enlarged scale;

FIG. 3 is a side, elevational view of the middle tube or cylinder of the device shown in FIG. 1, drawn to an enlarged scale;

FIG. 4 is a partially exploded, side, elevational view of the inner member or cylinder of the device shown in FIG. 1, drawn to an enlarged scale;

FIG. 5 is a side, elevational view of an additional, elongate surgical instrument which may be inserted through the inner member illustrated in FIG. 4;

FIG. 10 is a side elevational, enlarged scale, partial sectional view of the forceps or distal end of the invention;

FIG. 11 is a view similar to FIG. 10, but showing other instruments extended from the distal end of the device;

FIG. 12 is a partial elevational view of an embodiment of the invention having a tissue receiving slot formed in the distal end of the middle tubular member;

FIG. 13 is a view similar to FIG. 12 but showing a pair of slots formed in the middle member distal end;

FIG. 14 is a view similar to FIG. 13 but drawn to an enlarged scale and illustrating one embodiment of a stretchable clip of this invention mounted on the distal end of the middle member;

FIG. 15A is a perspective view of the stretchable clip illustrated in FIG. 14;

FIG. 15B is an elevational view showing the clip illustrated in FIG. 15A occluding a tubular anatomical structure such as a Fallopian tube;

FIGS. 24 through 39 are side elevational views, with parts broken away, of different types of forceps mounted on the distal end of the inner tubular member of a surgical device of the present invention;

FIGS. 40 and 41 are side elevational views, with parts broken away, of end and side suction devices, respectively, on the distal end of the inner tubular member of the present invention;

FIG. 42 is a side elevational view of a plug for the utero-tubal junction constructed in accordance with the principles of the present invention;

FIG. 43 is a side elevational view, with parts broken away, of a further embodiment of the surgical device of the present invention, with the utero-tubal junction plug removably mounted thereon;

FIG. 44 is an exploded side elevational view, showing the surgical device of FIG. 43, the plug of FIG. 42 and a pushing device for mounting the plug on the surgical device;

FIG. 45 is a side elevational view of a needle construction that can be used in conjunction with the surgical device shown in FIGS. 43 and 44;

FIGS. 46 and 47 are plan views, with parts broken away, showing a hysteroscopic plug and a laparoscopic plug, respectively, inserted in the utero-tubal junction;

FIG. 48 is a side elevational view of a fimbrial cap constructed in accordance with the principles of the present invention;

FIG. 49 is a front elevational view of the fimbrial cap shown in FIG. 48;

FIG. 50 is a side elevational view, with parts broken away, of another embodiment of the surgical device of the present invention, with the fimbrial cap removably mounted thereon;

FIGS. 51, 52 and 53 are perspective views of the fimbrial cap, the rear portion thereof and the front portion thereof, respectively, shown in FIG. 48;

FIG. 54 is a perspective view of the fimbria at the entrance of the Fallopian tubes; and FIG. 55 is a perspective view showing the fimbrial cap positioned over the fimbria shown in FIG. 54.

DESCRIPTION OF THE PREFERRED EMBODIMENTS

Figure 6:
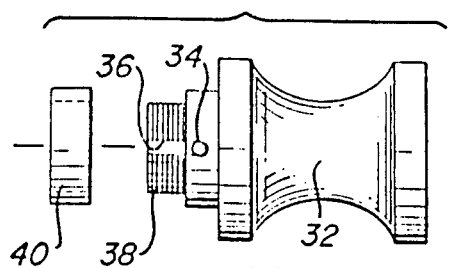
FIG. 6 is an exploded, bottom view of a handle which is used to extend and retract a forceps, the view being taken from the center portion of FIG. 1 and drawn to an enlarged scale.

Referring now to the drawings by reference character and, in particular, to FIGS. 1-4 thereof, a preferred embodiment of the surgical device 10 is shown, configured to apply either an elastic ring or stretchable clip onto a tubular, anatomical structure. Surgical device 10 includes an inner tubular member 12 which is slidably, telescopically received within a middle, tubular member 14 which, in turn, is telescopically, slidably received within an outer, tubular member 16. Each tubular member 12, 14 and 16 has a distal end 18, 20 and 22 and a proximal end 24, 26 and 28, respectively. Inner tubular member 12 has a forceps 30 of any desired construction extending from its distal end 18. The inner tubular member 12 may be of unitary construction or may be of two-piece telescoping construction to prevent the proximal end thereof from extending out of the proximal end of the device 10 in certain applications. Forceps 30 are extended from and retracted into distal end 20 of middle tubular member 14 by sliding inner tubular member 12 within middle tubular member 14. This is accomplished by moving a surrounding handle 32 which engages a peg 34 which depends from a mesial portion of inner tubular member 12, as is best illustrated in FIG. 4. The term "forceps" in the present application is intended to cover any type of gripping or holding means including suction means or the like.

The structure of handle 32 is best shown in FIG. 6. A slot 36 is formed at the forward end 38 of handle 32 and peg 34 is trapped therein by a cap 40 threaded onto end 38. Referring to FIG. 3, middle tubular member 14 has a elongated slot 42 formed in the bottom thereof and outer tubular member 16 has a similar slot 44 formed in the bottom thereof. Slots 42 and 44 have, generally, the same dimensions ad peg 34 extends through slots 42, 44 as can be appreciated from FIG. 1. Thus, movement of handle 32 back and forth effects extension and retraction of forceps 30 from distal end 20 of middle tube 14.

In order to accomplish an electrical cauterization procedure, peg 34 may also be a bipolar or unipolar electrical connector. Inner tubular member 12 may include an additional electrical connector 46 which is shown at the upper right hand portion of FIG. 1. Connector 46 may be a unipolar or bipolar electrical connector.

Proximal end 24 of member 12 may be threaded to receive an additional tubular segment 48 which may be provided with a stop cock 50 and a port 52. Port 52 may be connected, for example, to a pressurized supply of an inert gas such as carbon dioxide (not shown). Obviously, the gas will pass through the tubular member 12 to the surgical field. After the gas is introduced, stop cock 50 is closed to prevent the escape of the gas.

Turning now to FIG. 5, an instrument is illustrated which may be inserted through proximal end 24 of inner tubular member 12, into the surgical field. This instrument may be in the form of an elongated needle or cannula 54, housed within a protective shield 56. This instrument may be provided to effect electrical cauterization. For example, end 58 of the instrument may be provided with a unipolar electrical connector 60. This instrument might also be used for the injection of anesthesia, application of an inert gas such as carbon dioxide into the surgical field, application of laser energy to the surgical field, or for other, known purposes.

With further reference to FIG. 1, a rotatable, threaded connector member 62 is located on outer tubular member 16 between distal end 22 and the handle 32 for the purpose of releasably securing the device 10 to a laparoscope (not shown) or the like.

Figure 7:
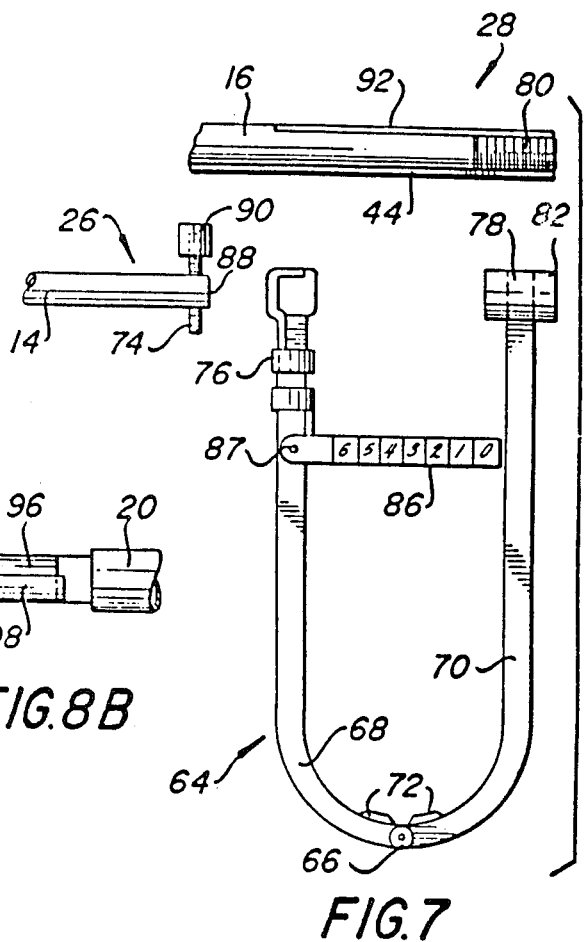
FIG. 7 is an elevational, exploded view taken from the right hand portion of FIG. 1 and drawn to an enlarged scale.

Referring now to FIG. 1, right hand portion, and FIG. 7, a handle structure is shown which is employed to eject a stretchable ligature from the distal end 20 of middle tubular member 14. A generally U-shaped handle 64 is provided which may be in one piece or may be centrally bifurcated at 66 into a first handle member 68 and a second handle member 70. Handle members 68 and 70 may be pivotally connected at the bifurcation point 66 and a spring 72 may be provided to urge members 68 and 70 apart.

With reference to FIG. 3, proximal end 26 of middle tubular member 14 includes a depending, threaded post 74. The upper end of handle member 68 is provided with an internally threaded member 76 for securing post 74 to the handle member 68. Of course, post 74 extends downwardly through the elongated slot 44 of outer tubular member 16. The upper end of second handle member 70 includes a capture ring 78 through which proximal end 28 of outer tubular member 16 is inserted. The proximal end 28 of tubular member 16 is externally threaded at 80 to receive an internally threaded capture cap 82. Thus, as handle 68 and 70 are squeezed together, distal end 22 of outer tubular member 16 moves towards and slides over the distal end 20 of middle tubular member 14, thus to eject a stretchable ligature mounted on distal end 20.

The methodology for accomplishing this is well disclosed in my prior U.S. Pat. No. 3,989,049. This patent discloses the eject of one or more elastic rings, such as is shown at 84 in FIG. 10. If multiple stretchable ligatures, plugs or caps are mounted on distal end 20, a gauge 86 may be provided which controls the movement of the outer tubular member 16 to eject the ligatures one at a time and to indicate the number of ligatures being ejected. The gauge may be mounted on either handle member 68 (FIG. 7) or handle member 70 (FIG. 1). The gauge may be pivotally mounted as is shown at 87 so that it may be swung out of the way if it is not to be used.

For further security of structure, proximal end 26 of middle tubular member 14 may be provided with a second, upstanding vertical post 88 having a head 90. Proximal end 28 of outer tubular member 16 would be provided with an upper, elongate slot 92 within which post 88 rides as outer tubular member 16 is moved axially relative to middle tubular member 14, to eject a stretchable ligature in the manner just described.

Figure 8A:
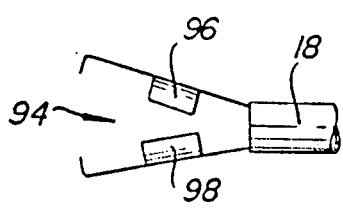
FIGS. 8A and 8B are partial, side, elevational views illustrating a modification of the invention shown in FIG. 1, wherein the forceps at the left of the view are provided with elements for taking a biopsy, FIG. 8A showing the instrument open and FIG. 8B showing the instrument closed.
Figure 8B:
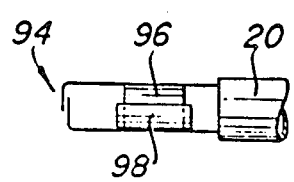

With reference to FIGS. 8A and 8B, a forceps structure is shown for taking a biopsy. An additional inner tubular member 12 is provided with forceps 94 having cooperating, biopsy box members 96 and 98. Retraction of forceps 94 in the manner described above causes the forceps to close and the biopsy box members 96 and 98 to cut and enclose a piece of tissue.

Figure 9:
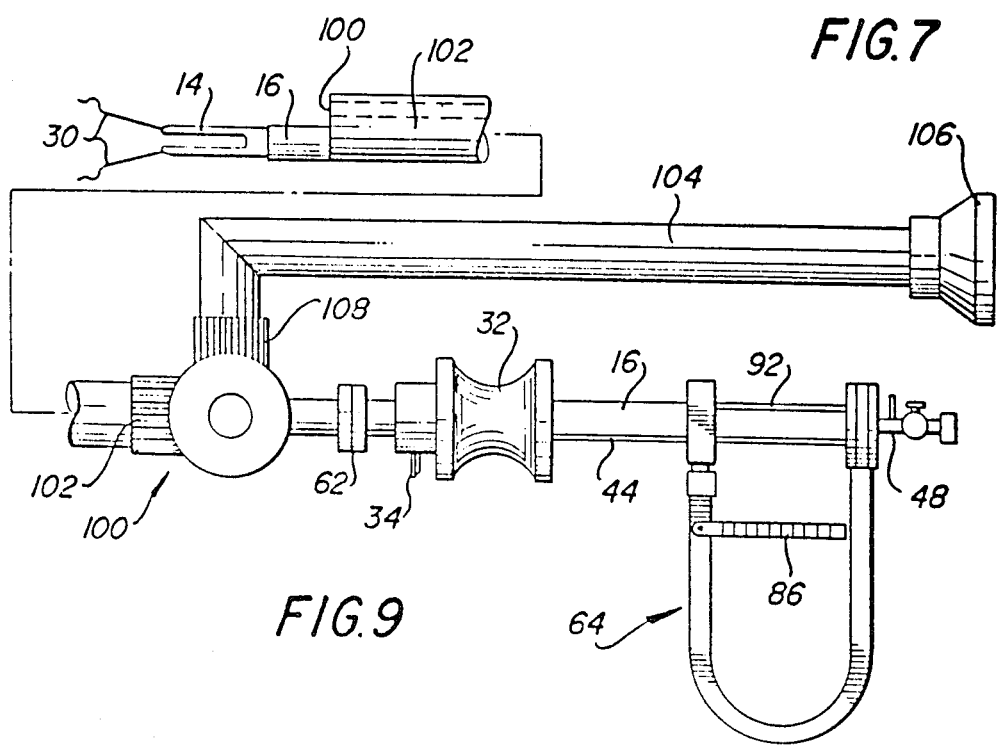
FIG. 9 is a side, elevational view of the device or instrument shown in FIG. 1 provided with a laparoscope, there being a swivel connection of the laparoscope with respect to the instrument.

With reference to FIG. 9, the instrument 10 of FIG. 1 is shown in combination with a laparoscope 100. Outer tubular member 16 is received with main body 102 of laparoscope 100. A light source is provided at 104. Laparoscope 100 includes an offset portion 104 having an eyepiece 106. Conveniently, offset portion 104 is connected to main body 102 by a swivel connection 108. Swivel connection 108 permits the offset portion 104 to be moved to a more comfortable position for the surgeon. More specifically, the surgeon need not stand directly behind the laparoscope but may more comfortably, view the surgical field from the side of the instrument.

FIG. 11 illustrates another forceps instrument for taking a biopsy, including cooperating cutting members 110 and 112.

As briefly discussed above and disclosed in extended detail in, for example, my prior U.S. Pat. Nos. 3,911,923 and 3,989,049, one method of applying a stretchable ligature to an anatomical tubular structure includes extending forceps 30 about the tube, withdrawing forceps 30 into proximal end 20 of middle tubular member 14 so as to crimp the tube and form a loop therein (e.g., as shown here in FIGS. 22 and 23) and then moving outer tubular member over middle tubular member 14 to eject a stretchable ligature (such as elastic member 84) onto and over the looped, anatomical tubular structure.

When the distal end 20 of middle tubular member 14 is completely closed, difficulty has been found in withdrawing an adequate amount of anatomical tubular structure into the device so as to assure effective occlusion of tissue upon placement of the stretchable ligature therearound. With reference to FIG. 12, a distal end 20 of middle tubular member 14 is illustrated having a tissue receiving slot 114 formed therein. Excess tissue may be located within the slot during the procedure so that an adequate amount of tubular structure is with-drawn into the middle tubular member 14. Also, the slot 114 allows the middle tubular member to expand somewhat to facilitate the entry of the tubular structure therein.

As shown in FIG. 13, a pair of tissue receiving slots 114, 116 are provided which have generally similar dimensions. This structure permits application of a stretchable ligature laterally across an anatomical tubular structure and thus eliminates the need for forming a loop in the tube being ligated. Depending on the type of forceps being utilized, the tissue may or may not be moved into the slots of the middle tubular member. For example, where forceps with overlapping ends are used, the tissue is moved to the distal end of the middle tubular member and the ligature is applied thereto without entry of the tissue into the slots. In the case of kissing forceps, the tissue may be moved into the slots before the ligature is applied thereto.

A first embodiment of a stretchable ligature of this invention is illustrated in FIG. 15A. This ligature includes a one-piece clip 118, formed of any non-tissue reactive, medical grade material that is suitable for implantation in the human body, having base portions 120, 122 and pairs of cooperating legs 124, 126. At least the base portions 120, 122 are made of a material having a sufficient elastic memory to force the pairs of legs 124, 126 closed after placement of the clip 118 over an anatomical tubular structure. Clip 118 is opened and forced over distal end 20 of middle tubular member 114 in a manner to be described below. This is shown in FIG. 14. Forceps 30 are then manipulated to grasp an anatomical tube and pull the same within the slots 114, 116. Outer tubular member 16 is then pushed over tubular member 14 to eject both clip 118 and the anatomical tubular tissue from the instrument. When ejected, the legs 124, 126 grasp and occlude the anatomical tubular structure under the urging of the base 120, 122. The result is illustrated in FIG. 15B.

Figure 16:
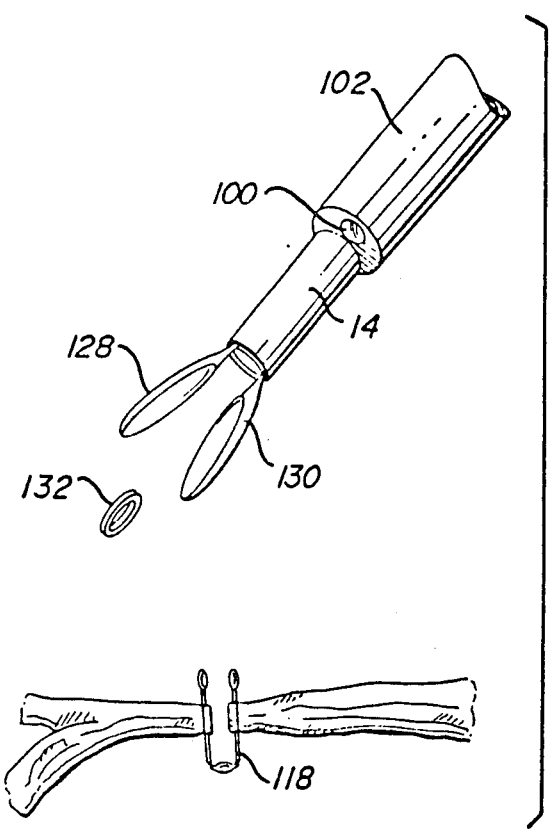
FIG. 16 is an elevational, exploded view illustrating placement of the clip shown in FIG. 15A and the further step of surgical removal of a segment of the anatomical tubular structure located between the legs of the clip.

When conducting a sterilization procedure and in order to assure a permanent sterilization, the section of tubular tissue between the legs 124, 126 may be severed and removed. This is illustrated in FIG. 16. After placement of clip 118 as described above, inner tubular member 12 may be replaced with another instrument having spring-loaded blades 128, 130 at the proximal end 18 of the member 12. The blades are brought together by retracting the member 12 within the intermediate tubular member 14, thus to sever a section 132 from the anatomical tubular structure. Thereafter, an instrument 54 (FIG. 5) can be inserted within the inner tubular member 12, the instrument 54 being connected to a source of suction (not shown). Instrument 54 is then extended into the surgical field and suction is applied to remove the excised piece 132.

Figure 17:
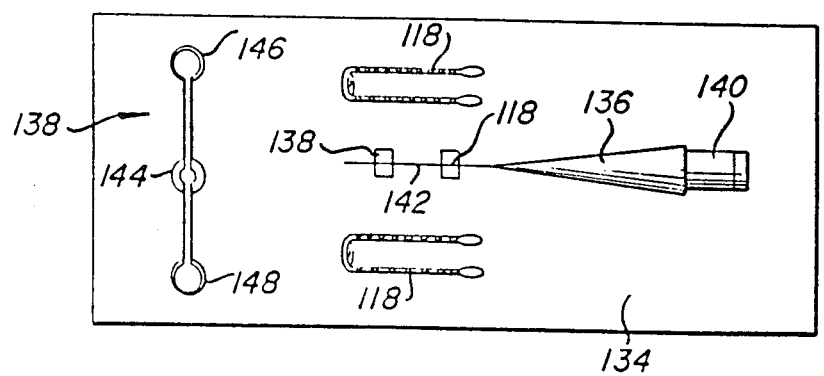
FIG. 17 is a plan view of a package of clips and the parts of a loading device for mounting the stretchable clip (FIG. 15A) onto the device (FIG. 14)

FIG. 17 illustrates a package 134 including a pair of clips 118, 118, a loading device 136 and a pushing device 138. In order to load a clip 118 onto distal end 20 of intermediate tubular member 14, end 140 of loading device 136 is inserted into the distal end 20. Clip 118 is slipped onto the narrowed end 142 of loading device 136. Pushing device 138 has a central aperture 144 and spring ends 146, 148. Pushing device 138 is inserted onto loading device 136 with end of 142 of loading device inserted through central aperture 144 of pushing device 138. The clip is then slid up the conical-shaped loading device 136 and pushed onto distal end 20 of intermediate tubular member 14. The result is illustrated in FIG. 14. Similar structure for loading an elastic ligature is disclosed in my prior U.S. Pat. Nos. 3,911,923 and 3,989,049.

Figure 18A:
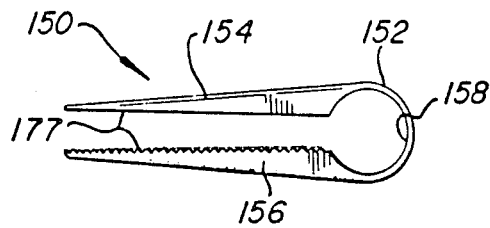
FIG. 18A is a side, elevational view of another stretchable clip of this invention in an open position.
Figure 18B:
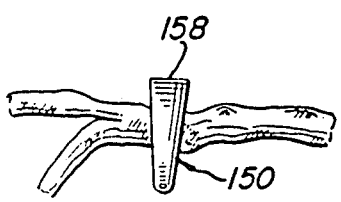
FIG. 18B shows the clip of FIG. 18A in place about an anatomical, tubular structure such as a Fallopian tube.

Other embodiments of the ligatures of this invention are illustrated in FIGS. 18-20 inclusive. In FIG. 18A, a clip 150 is shown including an elastic memory base 152 and a clamp portion in the form of a single pair of cooperating legs 154, 156. An opening 158 is formed in base 152 so that the clip 150 may be inserted onto proximal end 20 of intermediate tubular member 14 in the manner just discussed. FIG. 18B illustrates clip 150 after installation.

Figure 19A:
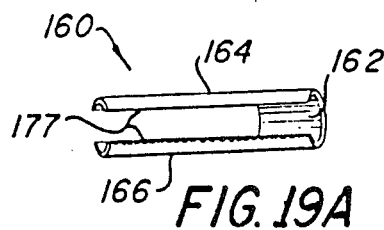
FIGS. 19A and 19B are views similar to FIGS. 18A and 18B, respectively, showing another embodiment of the stretchable clip of this invention.
Figure 19B:
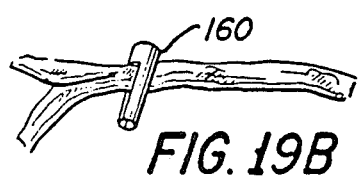

FIG. 19A shows a clip 160 having an elastic memory base 162 and opposed legs 164, 166. Base 162 may extend the full length of legs 164, 166 (not shown). Clip 160 is illustrated in place, ligating an anatomical tubular structure, in FIG. 19B.

Figure 20A:
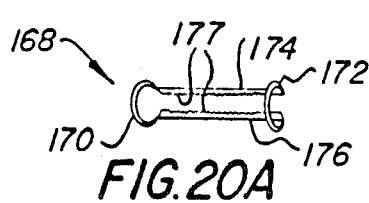
FIGS. 20A and 20B are views similar to FIGS. 18A and 18B, showing yet another embodiment of the stretchable clip of this invention.
Figure 20B:
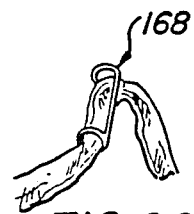

Another clip 168 is illustrated in FIG. 20A, including a pair of elastic memory bases 170, 172 joined by opposed legs 174, 176. FIG. 20B shows the clip 168 ligating an anatomical tubular structure.

If desired, the facing surfaces of the legs of each of the clips just discussed may be serrated as is shown at 177 in order to assure that the clip is securely locked onto the anatomical tubular structure being ligated.

Figure 21:
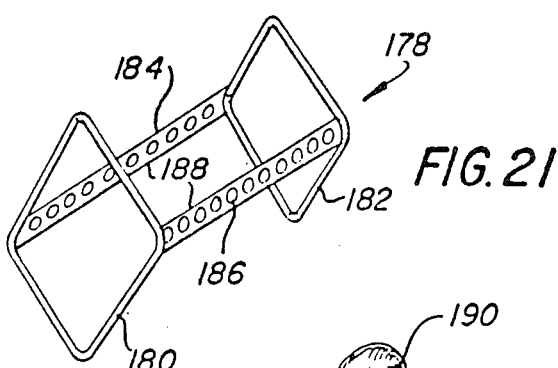
FIG. 21 is a perspective view showing yet another stretchable clip of this invention.
Figure 22:
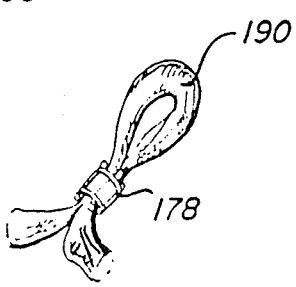
FIG. 22 is a perspective view showing one method of placement of the stretchable clip shown in FIG. 21.
Figure 23:
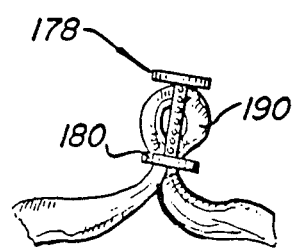
FIG. 23 is a perspective view showing another method of applying the stretchable clip illustrated in FIG. 21.

FIGS. 21-23 illustrates yet another stretchable ligature embodiment of this invention and two methods of placements of the ligature over and about an anatomical tubular structure. A clip 178 includes a pair of elastic memory bases 180, 182 which assume a quadrilateral configuration when forced open, as shown in FIG. 21. Bases 180, 182 are joined by a pair of legs 184, 186. The facing surfaces of the legs may be provided with rows of pins 188 which enhance locking of the clip 178 onto the tissue being occluded. As shown in FIG. 22, a large loop 190 is formed in the tissue being occluded and the clip 178 is applied well below the upper end of the loop 190. In FIG. 23, the clip is applied over the loop 190 with only the base 180 performing the occluding function.

The term "ligature" as generally used in this application is intended to cover members such as rings, clips, plugs or caps for anatomical tubular structures within the scope of the present invention.

Different types of forceps for mounting on the distal end of the inner tubular member 12 are shown in FIGS. 24 through 39. In accordance with the principles of the present invention, these modified forceps are mounted on inner tubular members which can be readily be interchanged with the tubular member 12 shown in FIG. 4, depending on the specific surgical application for the device 10 of the present invention. As illustrative examples, the forceps of FIGS. 24 and 25 have overlapping end portions when they are closed and are suitable for use with occluding rings, the kissing forceps of FIG. 27 and other figures are suitable for use with stretchable clips, the forceps of FIGS. 26 and 28 are provided with a hooked end portion, the forceps of FIGS. 29 and 30 are provided with recessed areas for holding a tubular structure or the like, the forceps of FIG. 31 are provided with four tongs; the forceps of FIGS. 32 and 35 are provided with portions for holding a biopsy specimen, and the forceps of FIGS. 33, 34, 36 and 37 are provided with needle-holding portions, alone or in combination with cutting or biopsy means.

Referring to FIGS. 40 and 41, the distal end of the inner tubular member 212 may be open at its end portion 213 (FIG. 40) or at a side portion 215 (FIG. 41) for the purpose of applying suction to hold a body member in place thereon.

As shown in FIGS. 42 through 47, the surgical device 10 of the present invention may be utilized to insert a plug or the like in the utero-tubal junction in a reversible sterilization procedure.

In a preferred embodiment, the plug 220 comprises a generally cylindrical base portion 222 and a plurality of flexible and resilient fingers 224 that are tapered to a pointed end portion and are normally closed, as shown in FIG. 42. In accordance with the operation of the surgical device 10 hereinbefore described, the plug 220 is mounted on the end portion of the inner tubular member 14 by being pushed thereon with a pusher device 226 of any desired construction. In this manner, the fingers 224 of the plug 220 are opened such that it is slidable over the middle tubular member 14 and is frictionally retained thereon, as shown in FIG. 43. Thereafter, the plug 220 may be inserted in the utero-tubal junction in a hysteroscopic procedure (FIG. 46) or a laparoscopic procedure (FIG. 47) by movement of the outer tubular member 16 into engagement with the base portion of the plug to push it off the middle tubular member 14 in a manner previously described herein. If desired, a needle 228 (FIG. 45) may be inserted through the middle tubular member 14 for the purpose of applying an anesthetic or the like during or before insertion of the plug 220 into the utero-tubal junction.

Referring to FIGS. 48 through 55, the surgical device 10 of the present invention can also be utilized to position a cap 230 over the fimbria 232 of the Fallopian tubes 234 in a reversible sterilization procedure. In a preferred embodiment, the cap 230 comprises an elongated, generally cylindrical body portion 236 with an elongated slit 238 therethrough so that the cap can be expanded for mounting on the end portion of the middle tubular member 14 in the manner shown in FIG. 50.

The cap 230 has an enlarged head portion 240 comprising a plurality of normally closed fingers 242 that are defined by transversed slots 244 in the head portion. The cap 230 is made of any suitable flexible and resilient material, such as a suitable plastic material so that the body portion 236 and head portion 240 thereof are normally closed in the manner shown in FIGS. 48, 49 and 51.

In operation, the body portion 236 and head portion 240 of the cap 230 are opened in any suitable manner to an extent such that the cap can be slidably and frictionally mounted on the distal end of the middle tubular member 14 of the surgical device 10 in the manner shown in FIG. 50. Through the use of suitable forceps 250 on the distal end of the inner tubular member 12, the tube 234 is grasped and then the cap 230 is positioned over the fimbria thereof, as shown in FIG. 55, by moving the outer cylinder 16 of the surgical device 10 into engagement with the head portion 240 of the cap 230 and pushing it off the middle tubular portion 14 in the manner previously described herein. It will be understood that the edges of the elongated slit 238 in the body portion 236 of the cap 230 engage the mesosalpink may be serrated or otherwise constructed to increase the gripping power of the cap on the mesosalpink when it is positioned over the tube 234 by the surgical device 10.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come from within the meaning and range of equivalency of the claims are therefore intended to be embraced therein.

I claim:

1. An anatomical tubular structure cap in the form of an integral, one-piece member, comprising: an elongated, tubular body portion having a longitudinal slit therethrough, and an enlarged head portion connected to said body portion, said head portion comprising a plurality of finger portions defined by transverse slits therein, said body portion and said head portion being formed of a flexible and resilient material such that the slits therein are normally closed.

2. The cap of claim 1 wherein the opposed surfaces of said body portion defining said slit are serrated.

3. The cap of claim 1 wherein said head portion is of a generally rounded shape.

* * * * *